United States Patent
Soukup

(10) Patent No.: US 8,207,352 B2
(45) Date of Patent: Jun. 26, 2012

(54) PROCESS FOR THE MANUFACTURE OF ENANTIOMERICALLY PURE ANTIFUNGAL AZOLES AS RAVUCONAZOLE AND ISAVUCONAZOLE

(75) Inventor: Milan Soukup, Sarasota, FL (US)

(73) Assignee: Drug Process Licensing Associates LLC, Dallas, TX (US)

( * ) Notice: Subject to any disclaimer, the term of this patent is extended or adjusted under 35 U.S.C. 154(b) by 115 days.

(21) Appl. No.: 12/587,488

(22) Filed: Oct. 8, 2009

(65) Prior Publication Data

US 2011/0087030 A1    Apr. 14, 2011

(51) Int. Cl.
*C07D 249/08*    (2006.01)
(52) U.S. Cl. .................................................... 548/266.6
(58) Field of Classification Search .................... None
See application file for complete search history.

(56) References Cited

U.S. PATENT DOCUMENTS

| 5,648,372 A | 7/1997 | Naito et al. |
| 5,686,646 A * | 11/1997 | Andrews et al. ................ 560/29 |
| 5,746,840 A * | 5/1998 | Willemsens et al. ......... 548/257 |
| 5,792,781 A | 8/1998 | Naito et al. |
| 6,020,497 A | 2/2000 | Farr et al. |
| 6,133,485 A | 10/2000 | Singh et al. |
| 6,300,353 B1 | 10/2001 | Hayase et al. |
| 6,383,233 B1 | 5/2002 | Reuter |
| 6,812,238 B1 * | 11/2004 | Fukuda et al. ................ 514/342 |
| 7,151,182 B2 * | 12/2006 | Fukuda et al. ................ 546/309 |
| 7,803,949 B2 * | 9/2010 | Sasho et al. ................... 548/112 |
| 2003/0236419 A1 | 12/2003 | Wang et al. |
| 2004/0176432 A1 | 9/2004 | Soukup |

FOREIGN PATENT DOCUMENTS

WO    WO 03002498 A1 *  1/2003

OTHER PUBLICATIONS

Pesti et al, Organic Process Research & Development 2009, 13, pp. 716-728.*
Ueda et al., Bioorganic & Med. Chem. Letters, vol. 13 (2003) 3669-3672.*
Liu Xu, et al. Synthetic Communications, 39: 1611-1625 (2009).*

* cited by examiner

*Primary Examiner* — Kamal Saeed
*Assistant Examiner* — Nyeemah A Grazier

(57) ABSTRACT

A new technical process for preparation of enantiomerically pure antifungal compounds of formula I by resolution of the racemates has been disclosed.

6 Claims, No Drawings

PROCESS FOR THE MANUFACTURE OF ENANTIOMERICALLY PURE ANTIFUNGAL AZOLES AS RAVUCONAZOLE AND ISAVUCONAZOLE

BACKGROUND OF THE INVENTION

Azole derivatives of a general formula I, having the 2R,3R-configuration, wherein $R^1$, $R^2$ and $R^3$ represent, independently from one another, hydrogen, fluorine, chlorine or $CF_3$-group are valuable antifungal drugs for treatment of systemic mycoses and possess a excellent broad antifungal activity.

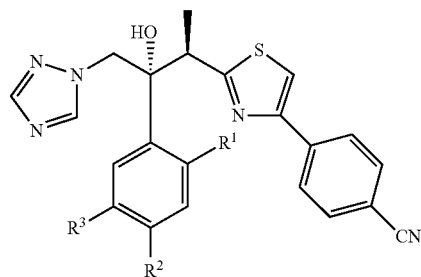

For example Isavuconazole [(2R,3R)-3-[4-(4-cyanophenyl)thiazol-2-yl)]-1-(1H-1,2,4-triazol-1-yl)-2-(2,5-difluorophenyl)-butan-2-ol; formula I, $R^1$ and $R^3$ represent fluorine and $R^2$ represents hydrogen] as well as Ravuconazole [(2R,3R)-3-[4-(4-cyanophenyl)thiazol-2-yl)]-1-(1H-1,2,4-triazol-1-yl)-2-(2,4-difluorophenyl)-butan-2-ol; formula I, $R^1$ and $R^2$ represent fluorine and $R^3$ represents hydrogen] are useful antifungal drugs as reported in U.S. Pat. No. 5,648,372 from Feb. 1, 1995 or in U.S. Pat. No. 5,792,781 from Sep. 18, 1996 or in U.S. Pat. No. 6,300,353 from Oct. 9, 2001 (WO99/45008).

Since compounds of general formula I contain two adjacent chiral centers, synthesis of enantiomerically pure compound is complex and until now, all patented syntheses are not efficient enough and do not allow cost effective manufacturing on a technical scale:

Thus, U.S. Pat. Nos. 5,648,372 or 5,792,781 describe enantioselective synthesis of compounds of formula I (specifically Ravuconazole) from chiral 3-hydroxy-2-methyl propionic acid in 12 steps with overall yield lower than 5%. In another approach including 13 steps and low overall yield, (R)-lactic acid was used as the starting material (Chem. Pharm. Bull. 46(4), 623 (1998) and ibid. 46(7), 1125 (1998)). Because both starting materials contain only one chiral center, in a number of inefficient steps, the second, adjacent chiral center has to be created by a diastereoselective reaction (using either Corey or Sharpless epoxidation method) which is not sufficiently selective leading mostly to a mixture of two diastereomers which have to be separated. The second approach, based on (R)-methyl lactate, was recently very thoroughly optimized by BMS on a multi kilogram scale but it still does not fulfill requirements for cost effective manufacturing process (Organic Process Research & Development 13, 716 (2009)). The overall yield of this optimized 11 steps process is still only 16% (Scheme 1).

Scheme 1:

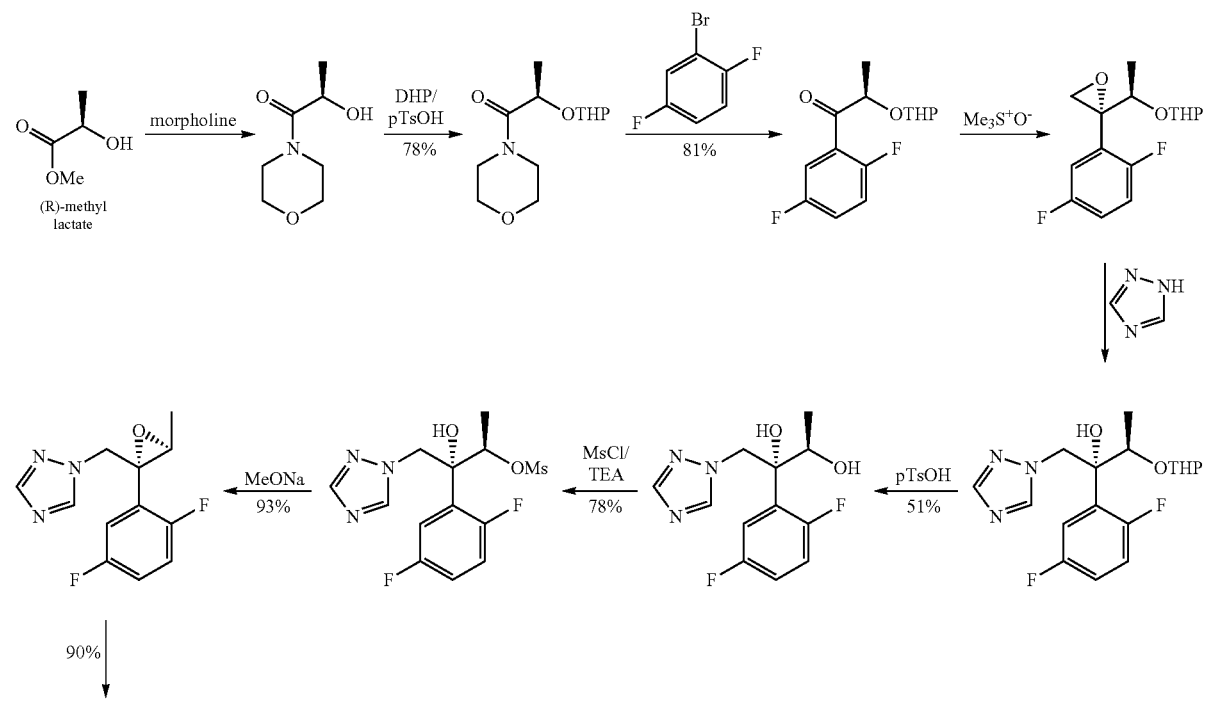

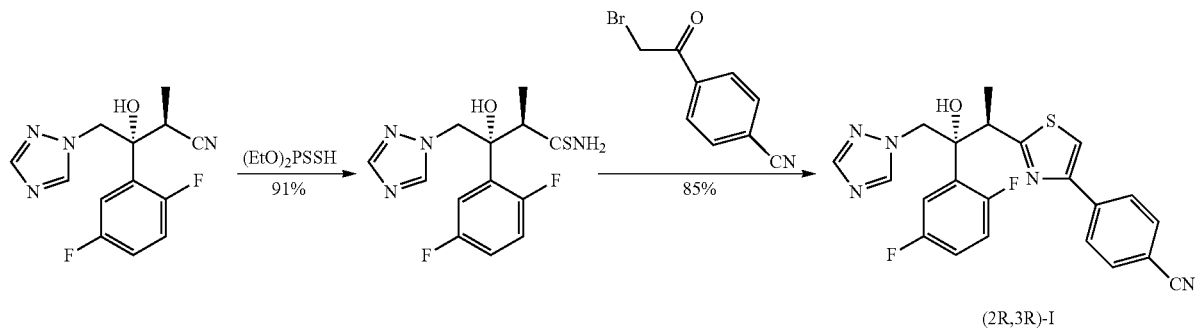

(2R,3R)-I

The manufacturing process for Isavuconazole is similar: Since Isavuconazole differentiates from Ravuconazole by only another fluorine substitution on the aromatic ring (2,5- instead of 2,4-difluorophenyl), the identical synthesis has been used (U.S. Pat. No. 6,300,353 from Oct. 9, 2001 and Bioorg. & Med. Chem. Lett. 13, 191 (2003)). Consequently, also this manufacturing process, based on (R)-lactic acid, faces the same problems: to many steps, extremely low overall yield and in addition to U.S. Pat. No. 6,300,353 claims even already known step as novel (claim 36).

Recent attempts to improve this concept as reported in WO 2007/062542 (Dec. 1, 2005), using less expensive, natural configured (S)-lactic acid, also failed: As already reported in U.S. Pat. No. 6,133,485 and in US 2003/0236419, the second chiral center was formed from an optically active allyl alcohol prepared in a few steps from (S)-lactic acid. This allyl alcohol was subjected to Sharpless diastereoselective epoxidation providing first an opposite configured, epimeric epoxy alcohol which had to be then epimerized in an additional inversion step yielding finally the desired epoxy alcohol as the known precursor for Isavuconazole (U.S. Pat. No. 6,300,353). It is obvious that this process using less expensive (S)-lactic acid makes the entire process with an inversion step even more complex than the original approach.

Elegant and more efficient process has been claimed in US 2004/0176432 from Jun. 26, 2001) in which both chiral centers have been formed simultaneously, diastereo- and enantio-selectively pure in one single reaction step using chiral (R)-2-butynol as a chiral precursor in the presence of Pd(II)-catalyst and diethyl zinc (Scheme 2).

Scheme 2:
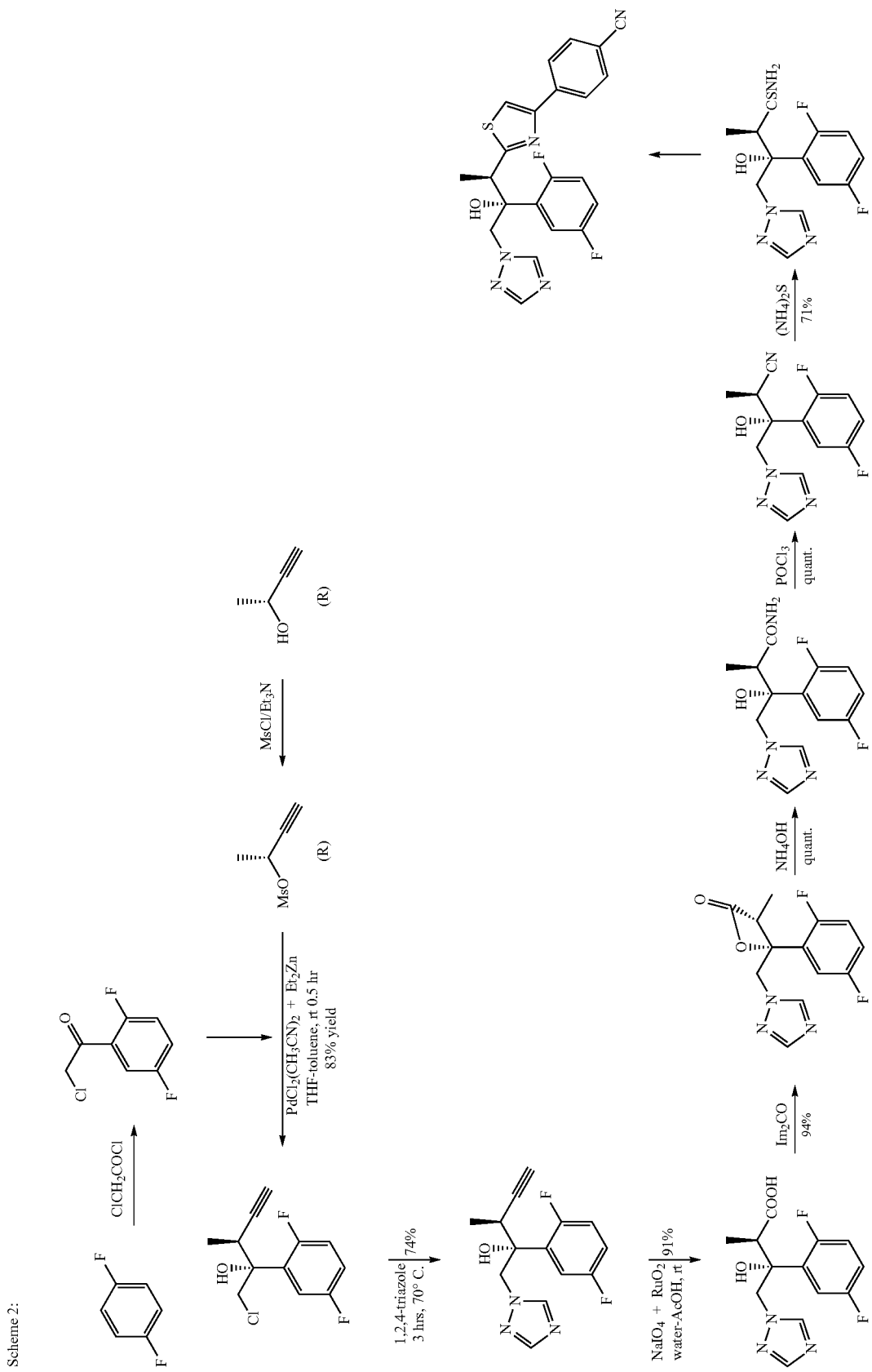

Since water soluble, (R)-2-butynol is expensive, recently identical process has been published, in which instead of (R)-2-butynol less water soluble and therefore, less expensive (R)-4-phenyl-3-butyn-2-ol was used (Synthetic Commun. 39, 1611 (2009)). Nevertheless, as incorrectly stated there, this process does not provide better diastereoselectivity than the original process using (R)-2-butynol: On the contrary disadvantage of this process is a very bad atom economy because huge phenyl group of (R)-4-phenyl-3-butyn-2-ol has to be "disposed" in oxidation step by the conversion of triple bond into carboxylic acid function.

All known processes for enantiomerically pure compounds of formula I have definitely too many operation steps and specifically very low overall yield. The chiral starting materials used, either 3-hydroxy-2-methyl propionic acid or (S)- or (R)-methyl lactate, contain only one chiral center and consequently, in number of steps, the second adjacent chiral center has to be ineffectively generated which makes the entire process long and expensive. The only known process, which generates both chiral centers simultaneously, requires again expensive chiral starting material (R)-2-butynol.

SUMMARY OF THE INVENTION

The present invention discloses a novel process for the manufacture of enantiomerically pure compounds of general formula I, specifically of Ravuconazole and Isavuconazole as shown in Scheme 3: Contrary to the previously claimed, inefficient enantioselective syntheses, according to this invention racemic compounds of general formula I or corresponding intermediates thereof (formulas II and III) have been initially prepared. These racemic compounds can be readily manufactured in high diastereomeric purity from known and inexpensive achiral starting materials in one or two simple steps by reaction of compounds of formula IV with either propionitrile or thioamides of general formula V. It has been now unexpectedly found that these racemic compounds of formula I, or the racemic intermediates thereof (formulas II and III), can be subjected to very efficient resolution step providing enantiomerically pure compounds of formula I; or alternatively enantiomerically pure intermediates thereof as formulas II and III, which can be readily converted into enantiomerically pure compounds of formula I.

Scheme 3:

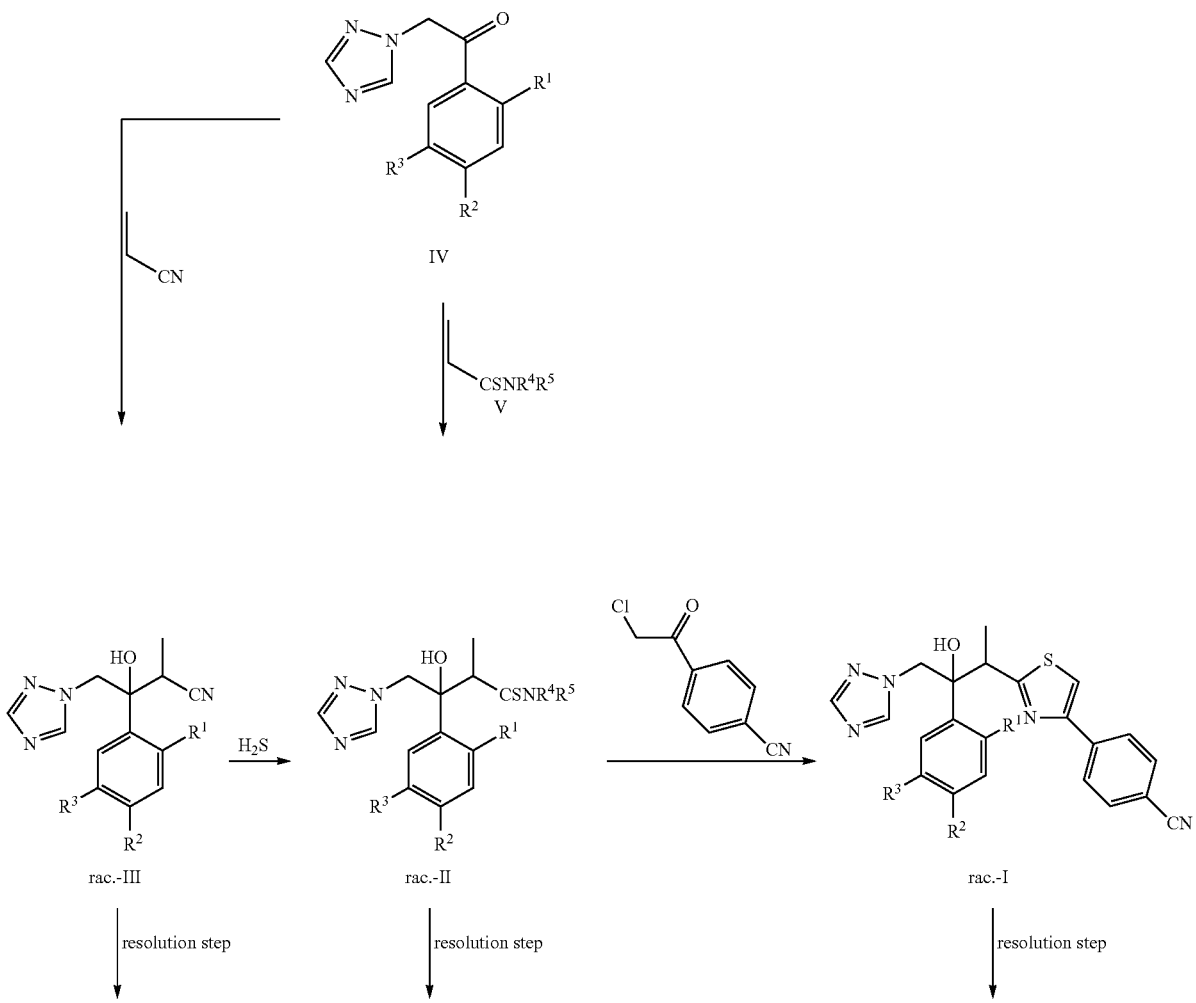

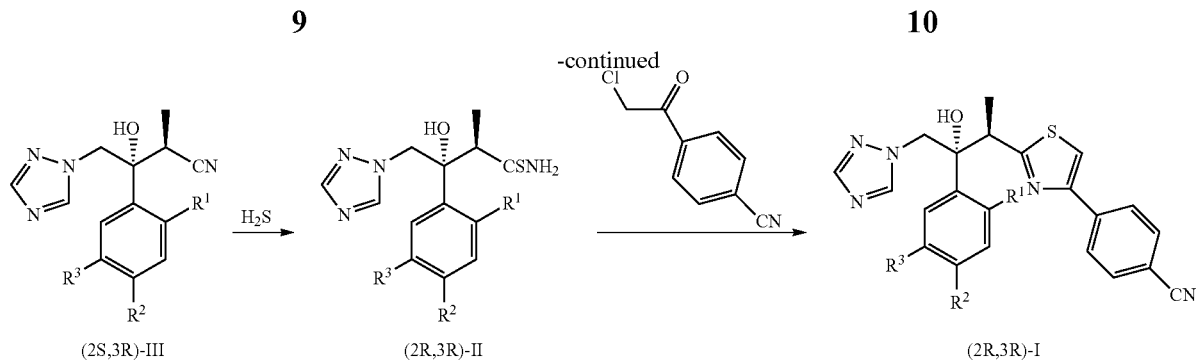

(2S,3R)-III     (2R,3R)-II     (2R,3R)-I

DETAILED DESCRIPTION OF THE INVENTION

The present invention claims a new process for the preparation of enantiomerically pure compounds of formula I, having the 2R,3R configuration,

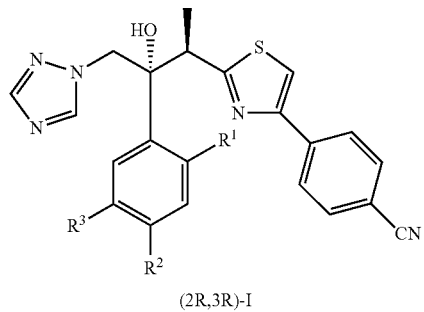

(2R,3R)-I wherein $R^1$, $R^2$ and $R^3$ represent, independently from one another, hydrogen, fluorine, chlorine or $CF_3$-group;
which comprises either
  a) a resolution step of the racemic compound of formula I, having the 2R/S, 3R/S configuration, by adding an appropriate chiral acid, crystallizing said mixture, collecting the desired diastereomeric salt of formula I either from the precipitate or from mother liquid and then converting the salt of formula I into an enantiomerically pure compound of formula I by treatment with an organic or inorganic base or using an ion-exchange resin
  or
  b) alternatively, a resolution step of the racemic compound of formula II, having the 2R/S, 3R/S configuration,

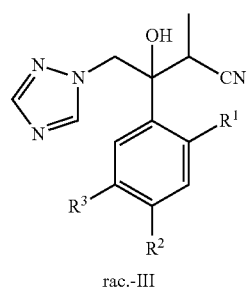

rac.-II wherein $R^1$, $R^2$ and $R^3$ are the same as defined for compound of formula I and wherein $R^4$ and $R^5$ represent, independently from one another, hydrogen, alkyl, aryl, alkylaryl, arylalkyl, alkoxy, aryloxy, arylalkoxy, alkylaryloxy, trialkylsilyl, alkylarylsilyl or with heteroatoms substituted alkyl, aryl, alkylaryl, arylalkyl, mono-, di- or tri-methoxybenzyl or
another for nitrogen known protective group, wherein $R^4$ and $R^5$ can also form together aliphatic or aromatic heterocyclic ring;
  by adding a chiral acid, crystallizing said mixture, collecting the desired diastereomeric salt of formula II either from the precipitate or from mother liquid and then either converting the salt of formula II into an enantiomerically pure compound of formula II by treatment with an organic or inorganic base or an ion-exchange resin, or alternatively using the salt of formula II directly, after removal of the nitrogen protective groups $R^4$ and $R^5$ in case $R^4$ and $R^5$ are not hydrogens, and reacting with 2-chloro-4'-cyanoacetophenone
  or
  c) alternatively, a resolution step of the racemic compound of formula III, having the 2S/R, 3R/S configuration,

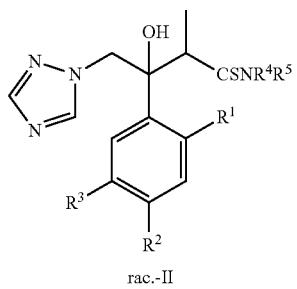

rac.-III wherein $R^1$, $R^2$ and $R^3$ are the same as defined for compound of formula I; by adding a chiral acid, crystallizing said mixture, collecting the desired diastereomeric salt of formula III either from the precipitate or from mother liquid and then either converting the salt of formula III into an enantiomerically pure form of the compound III by treatment with an organic or inorganic base or an ion-exchange resin, or using the salt of the formula III directly, reacting with hydrogen sulfide followed then by reaction of the resulting compound of formula II with 2-chloro-4'-cyanoacetophenone.

As the resulting agent any chiral acid, as commonly used for resolution of nitrogen containing compounds, can be used. Preferably acids as (1R or 1S)-10-camphorsulfonic acid or (D or L)-tartaric acid or (D or L)-dibenzoyl tartaric acid, (1R or 1S)-3-bromocamphor-10-sulfonic acid, (R or S)-1,1'-binaphtyl-2,2'-diyl-hydrogenphosphate itself or even in a mixture with another aliphatic or aromatic carboxylic acid, preferably glacial acetic acid can be used.

The chiral acid can be used in the amount of about 0.5 to 2 equivalents, preferably 0.7 to 1 eq. to the substrate.

The best results have been achieved specifically with (1R or 1S)-10-camphorsulfonic acid in a suitable solvent as e.g. water, acetone, butanone, propanone, ethylmethyl ketone, alcohols such as methanol, ethanol, isopropanol or their mixtures and more preferably mixtures of ketones with alcohols as e.g. acetone and methanol. Also aromatic solvents as benzene, toluene, xylene or halogenated derivatives thereof, but preferably toluene can be used. A recrystallization from an appropriate solvent may further be useful to increase the diastereomeric excess (% ee) of the crystalline diastereomeric salt.

A small addition of lower alkyl carboxylic acids, as preferably acetic acid (up to one equivalent) or even addition of water can significantly promote the crystallization of the salt and increase the ee value.

When the desired enantiomer is contained in the mother liquid, this isomer may be isolated following techniques known in the art: said technique comprises evaporation of the solvent(s), subsequent crystallization of the residue or optionally recrystallization and drying of the obtained crystals.

The separation process may also include all type of alternative separation techniques as e.g. emulsion crystallization or aggregate mixture crystallization in a tree phase system as e.g. reported in U.S. Pat. No. 2,182,025 B1 from May 7, 2002. Also preparative HPLC or SMB (simulated moving bed chromatography) can be used.

The salt of the resolving chiral acid can be converted into the free base with alkali metal hydroxides or carbonates or bicarbonates, preferably sodium or potassium hydroxide or carbonate or bicarbonate in a suitable organic solvent as methylenechloride, ethylacetate, TBME, diisopropylether or toluene or water. An ion exchange resin can also be used to liberate the free base using a polar solvent as alcohols, THF and water or mixtures thereof.

In an alternative resolution process b) the racemic thioamide of formula II can be resolved in the same way as described for compound of formula I: Preferably chiral acids as e.g. (1R or 1S)-10-camphorsulfonic acid or (D or L)-tartaric acid or (D or L)-dibenzoyl tartaric acid, (1R or 1S)-3-Bromocamphor-10-sulfonic acid, (R or S)-1,1'-binaphtyl-2,2'-diyl-hydrogen-phosphate can be used.

The racemic compound of formula II can be preferably primary thioamide, wherein $R^4$ and $R^5$ represent hydrogens, but also N,N-disubstituted thioamides of formula II can be used wherein $R^4$ and $R^5$ can be independently from one another alkyl, aryl, alkylaryl, arylalkyl, alkoxy, aryloxy, arylalkoxy, alkylaryloxy, trialkylsilyl, alkylarylsilyl or any with heteroatom(s) substituted alkyl, aryl alkylaryl, mono-, di- or tri-methoxybenzyl, preferably as N,N-diprotected thioamides as e.g. N,N-diallyl- or N,N-dibenzyl)- or N,N-bis-(2,4-dimethoxybenzyl) thioamide derivatives of formula II.

As N,N-diprotected thioamides $R^4$ and $R^5$ can also be another for nitrogen commonly used protective group(s), wherein $R^4$ and $R^5$ can form together aliphatic or aromatic heterocyclic ring system, preferably substituted isoxazolidines as e.g. reported in Tetrahedron Asymm. 1995, 6, 1295 or U.S. Pat. No. 6,020,497 (Feb. 1, 2000). In addition the N-protective group(s) can also contain a chiral center or centers to improve the diastereoselectivity or to facilitate the resolution of the racemate.

Groups $R^4$ and $R^5$ are preferably protective groups which can be readily removed by either simple hydrolysis or amminolysis or by a reductive process providing the unprotected primary thioamide of general formula II. When e.g. N,N-bis-(2,4-dimethoxybenzyl)-thioamide of formula II has been used, the N-protective groups can be readily removed reductively with triethylsilane in high yield in the presence of triflic or trifluoroacetic acid in methylenechloride at rt.

The enantiomerically pure thioamide of formula II, wherein $R^4$ and $R^5$ are preferably hydrogen(s) can also be isolated as a salt of strong mineral or organic acid, preferably as hydrogensulphate which can be then directly used for conversion into the final compound of formula I.

The enantiomerically pure thioamide of formula II, wherein $R^4$ and $R^5$ are hydrogens, having the 2R, 3R configuration, or salt thereof can be converted in the next step beneficially with less expensive 2-chloro-4'-cyanoacetophenone (J. Heterocycl. Chem. 43, 1608 (2006) or J. Am. Chem. Soc. 107, 2506 (1985)) into the final enantiomerically pure compound of formula I according to a standard procedure in boiling 2-propanol or methanol as published in J. Med. Chem. 33, 13, (1990) or Ind. J. Chem. 24B, 131 (1985).

In an alternative resolution process c) the racemic compound of formula III can be resolved in the same way as mentioned for compound of formula I. Preferably chiral acid as e.g. (1R or 1S)-10-camphorsulfonic acid or (D or L)-tartaric acid or (D or L)-dibenzoyl tartaric acid, (1R or 1S)-3-Bromocamphor-10-sulfonic acid, (R or S)-1,1'-binaphtyl-2,2'-diyl-hydrogenphosphate can be used.

The enantiomerically pure nitrile of formula III, having the 2S, 3R configuration, can be readily converted with hydrogen sulfide in a polar solvents as alcohols or water, preferably 2-propanol into the thioamide of general formula II which is further reacted with 2-chloro-4'-cyanoacetophenone, as described above, providing enantiomerically pure compound of formula I. Instead of hydrogen sulfide alternative reagents as e.g. ammonium sulfide or diethyl dithiophosphate can also be used.

The enantiomerically pure nitrile of formula III can also be isolated as a salt of a strong mineral or organic acid, preferably hydrogensulphate which can be then directly used for the 2 steps conversion into the final compound of formula I.

In alternative sequence the enantiomerically pure nitrile of formula II can be converted first into the corresponding amide which can be then reacted with Lawson's reagent providing the thioamide of formula II.

Instead of a resolution of a single racemic compound of formula I or II or III, also a diastereomeric mixture of two corresponding racemates can be used. Thus, by adding an appropriate chiral acid, crystallizing said mixture, the desired diastereomeric salt of formulas I or II or III either from the precipitate or from mother liquid can be collected and then converted into an enantiomerically pure form of the compound of formulas I or II or III by treatment with an organic or inorganic base or using an ion-exchange resin.

The racemic compounds of formula I, II and III can be readily prepared according to Scheme 3 as explained below:

As reported in WO 92/17474 (Apr. 4, 1991) the racemic compound of formula III can be readily prepared from the compound of formula IV by reacting with propionitrile in the presence of a strong organic base. Thus, propionitrile has been first deprotonated in THF at −78° C. with a strong organic base, preferably butyllithium or LDA (Lithium diisopropyl amide) and the resulting mixture reacted then with compound of general formula IV. After acidification of the reaction mixture the racemic compound of formula III has been isolated in good yield. In most cases another diastereomer of formula III has not been formed.

The addition reaction is typically carried out from −78° C. to −50° C. under inert atmosphere. In some cases it can be advantageous to treat the intermediary tert. alcoholate formed in situ with chlorotrialkylsilene e.g. TMS-Cl or alkyl chloroformate to prevent the retro-addition reaction during the work-up at elevated temperate. The O-protective group, carbonate or TMS, are readily removed during the acidic workup.

To increase the yield an excess up to 10 equivalents of propionitrile and consequently, the base used is beneficial.

The choice of solvent can be critical, in some cases, instead of THF toluene or a mixture with THF can be preferred.

Preferably 1-(2,4-difluorophenyl)-2-(1H-1,2,4-triazol-1-yl)ethanone or 1-(2,5-difluorophenyl)-2-(1H-1,2,4-triazol-1-yl)ethanone has been used and condensed with propionitrile after prior deprotonation with LDA or butyllithium in THF at −78° C.

The compound of general formula IV has been prepared from substituted benzene, preferably mono-, difluoro- or trifluoro-benzene etc. by Friedel-Crafts reaction with chloroacetylchloride in the presence of Lewis acid as aluminum chloride or bortrifluor etherate followed by reaction with 1,2,4-triazole in THF or other organic solvents in the presence of base, preferably alkali alkoxide as sodium tert-butoxide or even sodium hydride.

The racemic compound of formula III can be either subjected to the resolution step as claimed above or reacted first with hydrogen sulphide and then 2-chloro-4'-cyanoacetophenone providing the racemic compound of formula I which can be then resolved.

As reported at Colorado Symposium on Synthetic Organic Chemistry in Bolder (CO) in 2002 the racemic compound of formula II can be readily prepared from compound of formula IV reacting in aprotic solvents in the presence of strong inorganic or organic base with thioamide of formula V,

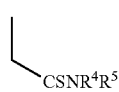

wherein $R^4$ and $R^5$ are the same as defined above for compound of formula II. Thioamides of formula V can be easily deprotonated in THF at −78° C. with strong organic base, preferably butyllithium, LDA or lithium- or sodium-hexamethyldisilazane and then reacted with compound of formula IV. After acidification of the reaction mixture the racemic compound of formula III can be isolated in very high yield >85% as a single diastereomer.

The choice of solvent can be critical, in some cases instead of THF toluene or a mixture with THF is preferred.

In some cases addition of dried 0.1-1 equiv. Lewis acid as e.g. Cerium trichloride prior addition of compound IV can significantly increase the yield.

A slight excess (2-3 equivalents) of compound of formula V and the base used can be beneficial.

Preferably 1-(2,4-difluorophenyl)-2-(1H-1,2,4-triazol-1-yl)ethanone or 1-(2,5-difluorophenyl)-2-(1H-1,2,4-triazol-1-yl)ethanone has been used and condensed with compound of formula V after prior deprotonation with LDA or butyllithium in THF at −78° C.

Thioamides of formula V can be prepared either by reaction of commercially available methyl dithiopropionate with amine $HNR^4R^5$, wherein $R^4$ and $R^5$ are identical with $R^4$ and $R^5$ as defined for the formula II and V or alternatively via the amides using Lawesson reagent.

Groups $R^4$ and $R^5$ are protective groups as described above for compound of formula II.

The racemic compounds of formula II can be either subjected to the resolution step as described above for compound of formula I or reacted first with 2-chloro-4'-cyanoacetophenone providing the racemic compound of formula I which is then subjected to the resolution step as described above for compound of formula I.

The undesired enantiomers of formula 2S,3S-II or formula 2R,3S-III can be subjected to a treatment with strong base in organic solvent, preferably sodium hydride in THF providing in a retro-addition reaction starting compound of formula IV which can be recycled.

The example are provided to illustrate particular aspects of the disclosure and do not limit the scope of the present invention as defined by the claims.

EXAMPLES

Determination of optical purity was carried out with HPLC using chiral columns as Chiralcel OJ-H, Chiralpak AS-H or Chiralpak AD-H from Daicel Chem. Ind.

In some cases the optical purity was also determined with NMR-Spectroscopy using chiral Eu-shift reagent.

Example 1

(2R,3R)-3-[4-(4-cyanophenyl)thiazol-2-yl]-1-(1H-1,2,4-triazol-1-yl)-2-(2,4-difluorophenyl)-butan-2-ol To a solution of racemic 3-[4-(4-cyanophenyl)thiazol-2-yl]-1-(1H-1,2,4-triazol-1-yl)-2-(2,4-difluorophenyl)-butan-2-ol (43.7 g) in acetone (800 ml) a solution of (1R)-10-camphorsulfonic acid (23 g) in methanol (300 ml) was added and the mixture was heated under reflux until a clear solution was obtained. The solution was slowly cooled to rt, seeded with crystals of the title enantiomeric salt and let overnight. The solid was collected by filtration, washed with acetone and dried to provide (2R,3R)-3-[4-(4-cyanophenyl)thiazol-2-yl]-1-(1H-1,2,4-triazol-1-yl)-2-(2,4-difluorophenyl)-butan-2-ol (1R)-10-camphorsulfonate as white solid. This crude salt was then taken up in methylenechloride (100 ml) and water (ca. 100 ml) and the mixture was basified with aqueous sodium hydroxide solution. The organic layer was separated and the aqueous phase washed twice with methylenechloride (50 ml) and combined. The organic phases were then washed twice with water (2×50 ml), dried with sodium sulfate, filtrated and the solvent removed under reduced pressure. The crude product was then mixed with isopropanol (ca. 150 ml), heated for 10 min, cooled to 0° C. and stirred for ca. 2 hrs. The product was collected, washed with isopropanol and dried under reduced pressure to provide the enantiomerically pure title compound (17.5 g, 41% yield, 99.1% ee); m.p. 164-166° C.; [α]=−30° (c=1, methanol, 25° C.); NMR (CDCl3): 1.23 (3H, d, J=8 Hz), 4.09 (1H, q, J=8 Hz), 4.26 (1H, d, J=14 Hz), 4.92 (1H, d, J=14 Hz), 5.75 (1H, s), 6.75-6.85 (2H, m), 7.45-7.54 (2H, m), 7.62 (1H, s), 7.69 (1H, s), 7.75 (1H, d, J=8 Hz), 7.86 (1H, s), 8.03 (1H, d, J=8 Hz). The analytical data were identical with published (U.S. Pat. No. 5,648,372 and Chem. Pharm. Bull. 1998, 46, 623-630).

Example 2

(2R,3R)-3-[4-(4-cyanophenyl)thiazol-2-yl]-1-(1H-1,2,4-triazol-1-yl)-2-(2,4-difluorophenyl)-butan-2-ol Racemic 3-[4-(4-cyanophenyl)thiazol-2-yl]-1-(1H-1,2,4-triazol-1-yl)-2-(2,4-difluorophenyl)-butan-2-ol (44 g) and (1R)-10-camphorsulfonic acid (20 g) were suspended in methanol (ca. 300 ml), the slurry was stirred intensively, warmed up to ca. 70° C. and a small addition of acetic acid was added to obtain a clear solution. After cooling of the solution to rt and then to 0° C., the mixture was seeded with enantiomerically pure salt and stirred for another 2 hrs. The crystalline solid was collected by filtration, washed with cooled methanol and dried under reduced pressure. The crystals were partitioned between methylenechloride (300 ml) and saturated aqueous sodium bicarbonate solution (200 ml). The organic layer was washed twice with water (50 ml), dried with magnesium sulphate, filtrated and evaporated under reduced pressure to give the title compound (16.9 g, 38% yield, 95% ee). The analytical data were identical with published (U.S. Pat. No. 5,648,372 or Chem. Pharm. Bull. 1998, 46, 623).

Example 3

(2R,3R)-3-[4-(4-cyanophenyl)thiazol-2-yl]-1-(1H-1,2,4-triazol-1-yl)-2-(2,5-difluorophenyl)-butan-2-ol To a solution of racemic 3-[4-(4-cyanophenyl)thiazol-2-yl]-1-(1H-1,2,4-triazol-1-yl)-2-(2,5-difluorophenyl)-butan-2-ol (10 g) in acetone (ca. 200 ml) a solution of (1R)-10-camphorsulfonic acid (3.9 g) in methanol (50 ml) was added and the mixture was heated shortly under reflux until a clear solution was obtained. The solution was then slowly cooled to rt, seeded with crystals of the desired enantiomeric salt and let overnight. The solid precipitate was collected by filtration, washed with acetone and dried to provide (2R,3R)-3-[4-(4-cyanophenyl)thiazol-2-yl]-1-(1H-1,2,4-triazol-1-yl)-2-(2,5-difluorophenyl)-butan-2-ol (1R)-10-camphorsulfonate as white solid. This salt was then taken up in methylenechloride and water and basified with aqueous sodium bicarbonate solution. The organic layer was separated and the aqueous phase washed twice with methylenechloride. The organic phases were combined, dried with sodium sulphate, filtrated and the solvent removed under reduced pressure. The crude product was then dissolved in ethanol, the slurry heated for 20 min, small amount of water was added, the solution slowly cooled to 0° C. and stirred for ca. 2 hrs. The product was collected, washed with cold ethanol and dried under reduced pressure to provide the title enantiomerically pure compound (3.9 g, 39% yield, 96% ee). The analytical date were identical with published in U.S. Pat. No. 6,300,353 B1 and WO 99/45008.

Example 4

(2R,3R)-3-[4-(4-cyanophenyl)thiazol-2-yl]-1-(1H-1,2,4-triazol-1-yl)-2-(2,5-difluorophenyl)-butan-2-ol To a solution of racemic 3-[4-(4-cyanophenyl)thiazol-2-yl]-1-(1H-1,2,4-triazol-1-yl)-2-(2,5-difluorophenyl)-butan-2-ol (100 g) in acetone (1000 ml) a solution of (1R)-10-camphorsulfonic acid (47 g) in methanol (500 ml) was added at rt, then slurry was heated under stirring to almost reflux for ca. 30 min, then cooled slowly to rt, seeded with the pure enantiomeric salt and stirred over night. The solid was collected by filtration, washed with methanol/acetone mixture, dried under reduced pressure. The residue was taken up with a solvent mixture of methylenechloride/water and after addition of saturated aqueous sodium bicarbonate solution the organic phase was separated and aqueous phase washed twice with methylenechloride. The combined organic phases were filtrated, the solvent removed under reduced pressure. Recrystallization of the crude product from aqueous ethanol provided enantiomerically pure title compound: 39 g (39% yield, 92% ee). The analytical data were identical with published: U.S. Pat. No. 6,300,353 and WO 99/45008.

Example 5

(2R,3R)-3-[4-(4-cyanophenyl)thiazol-2-yl]-1-(1H-1,2,4-triazol-1-yl)-2-(2,5-difluorophenyl)-butan-2-ol A solution of the racemic 3-[4-(4-cyanophenyl)thiazol-2-yl]-1-(1H-1,2,4-triazol-1-yl)-2-(2,5-difluorophenyl)-butan-2-ol (4.4 g) and (1R)-10-camphorsulfonic acid (2 g) in toluene (40 ml) containing glacial acetic acid (0.6 ml) was warmed up to approximately 70° C., then allowed to cool slowly to 20° C., seeded with the pure enantiomeric salt whereupon the pure enantiomeric salt start to crystallize out. After ca. 2 hrs at this temperature the solid was collected, washed with cold toluene and dried. The crystals were taken with a solvent mixture of methylenechloride/water and after addition of aqueous saturated sodium bicarbonate solution the organic phase was separated and aqueous phase washed twice with methylenechloride. The combined organic phases were filtrated and the solvent removed under reduced pressure. Recrystallization of the crude product from aqueous ethanol provided enantiomerically pure title compound: 2 g (45% yield, 99% ee). The analytical data were identical with published: U.S. Pat. No. 6,300,353 and WO 99/45008.

Example 6

(2S,3R)-3-(2,5-difluorophenyl)-3-hydroxy-2-methyl-4-(1H-1,2,4-triazol-1-yl)butanenitrile To a solution of racemic 3-(2,5-difluorophenyl)-3-hydroxy-2-methyl-4-(1H-1,2,4-triazol-1-yl)butanenitrile (2.7 g) in acetone (40 ml) a solution of (1R)-10-camphorsulfonic acid (2 g) in methanol (30 ml) was added and the mixture was heated under reflux until a solution was obtained. The solution was slowly cooled to rt, seeded with crystals of the desired enantiomeric salt and let overnight. The solid was collected by filtration, washed with small amount of cold acetone and dried to provide (2S,3R)-3-(2,5-difluorophenyl)-3-hydroxy-2-methyl-4-(1H-1,2,4-triazol-1-yl)butanenitrile-(1R)-10-camphorsulfonate as white solid. This salt was taken up in methylenechloride (20 ml) and water (ca. 30 ml) and the mixture was basified with aqueous sodium hydroxide solution. The organic layer was separated and the aqueous phase washed twice with methylenechloride (50 ml) and combined. The organic phases were then washed with water (2×30 ml), dried with sodium sulfate, filtrated and the solvent removed under reduced pressure. The crude product was then mixed with isopropanol (20 ml), heated for 10 min, cooled to 0° C. and stirred for ca. 2 hrs. The product was collected, washed with aqueous isopropanol and dried under reduced pressure to provide the enantiomerically pure title compound (1.05 g, 38% yield, 99% ee). The analytical data were identical with published: U.S. Pat. No. 6,300,353 and WO 99/45008.

Example 7

(2R,3R)-3-[4-(4-cyanophenyl)thiazol-2-yl]-1-(1H-1,2,4-triazol-1-yl)-2-(2,5-difluorophenyl)-butan-2-ol from (2S,3R)-3-(2,5-difluorophenyl)-3-hydroxy-2-methyl-4-(1H-1,2,4-triazol-1-yl)butanenitrile In a autoclave to a solution of (2S,3R)-3-(2,5-difluorophenyl)-3-hydroxy-2-methyl-4-(1H-1,2,4-triazol-1-yl)butanenitrile (2.8 g) in ethanol (10 ml) concentrated sulphuric acid (1 g) was slowly added, the autoclave was closed and a slight pressure of hydrogen sulphide was introduced over the solution. After heating the reaction mixture in closed autoclave for 5 hrs, the autoclave was cooled to rt, excess of hydrogen sulphite was discharged and the crude mixture poured on a mixture of methylenechloride (100 ml) and water (100 ml). The water phase was extracted 3 times with methylenechloride (100 ml) and the organic phase washed once with water, dried with sodium sulphate and after addition of MTBE (50 ml) concentrated under reduced pressure to volume of ca. 75 ml. The slurry was then hold for 5 hrs at 0° C., the precipitate collected by filtration, the crystals washed with MTBE, dried in vacuum providing a hydrogensulphate salt of (2R,3R)-3-(2,5-difluorophenyl)-3-hydroxy-2-methyl-4-(1H-1,2,4-triazol-1-yl)thioburyramide. This salt was then dissolved in ethanol (20 ml), 2-chloro-4"-cyanoacetophenone (1.8 g) was added and the reaction mixture heated to 60-70° C. for 8 hrs until the reaction was completed. At this temperature after addition of water (30 ml) the pH of the solution was adjusted with triethylamine to ca. pH 4-5, the solution cooled to rt and stirred for 5 hrs, the crystals collected, washed with 50% ethanol-water solution, dried in vacuum at 50° C. to yield the title compound as a white crystals (3.5 g, 81% yield). The analytical data were identical with published: U.S. Pat. No. 6,300,353 and WO 99/45008.

Example 8

(2R,3R)-3-(2,4-difluorophenyl)-3-hydroxy-2-methyl-4-(1H-1,2,4-triazol-1-yl)thioburyramide A solution of the racemic 3-(2,4-difluorophenyl)-3-hydroxy-2-methyl-4-(1H-1,2,4-triazol-1-yl)thioburyramide (31 g) and (1R)-10-camphorsulfonic acid (23 g) in toluene (400 ml) containing glacial acetic acid (0.6 ml) was heated to approximately 70° C., the solution was allowed to cool slowly to 20° C., seeded with the desired salt whereupon the pure enantiomeric salt crystallizes out. After ca. 1 hr at this temperature the solid was collected, washed with cold toluene and dried. The crystals were taken with a solvent mixture of methylenechloride/water and after addition of saturated aqueous sodium bicarbonate solution the organic phase was separated and the aqueous phase washed twice with methylenechloride. The combined organic phases were filtrated and the solvent removed under reduced pressure. Recrystallization of the crude product from aqueous ethanol provided enantiomerically pure title compound: 12 g (98% ee): m.p. 132-134° C.; [α]=−143.8° (c=0.15, methanol, 25° C.). The analytical date were identical with published (U.S. Pat. No. 5,648,372 or Chem. Pharm. Bull. 1998, 46, 623).

Example 9

3-(2,4-difluorophenyl-3-hydroxy-2-methyl-4-(1H)-1,2,4-triazol-1-yl)butanenitrile Propionitrile (55 g) was added over 30 min to a stirred solution of n-butyllithium (625 ml of 1.6 M solution in hexane) in dry THF (600 ml) at −78° C. under an atmosphere of dry nitrogen. The solution was then stirred for 20 min and a solution of 1-(2,4-difluorophenyl)-2-(1H-1,2,4-triazol-1-yl) ethanone (110 g) in dry THF (100 ml) was slowly added with stirring at a rate that the reaction temperature did not exceed −50° C. Stirring was continued at −78° C. for another 60 min and acetic acid (80 ml) was added, the reaction mixture was allowed to warm up to rt, poured on water (1000 ml), the aqueous phase extracted 4 times with ethylacetate (600 ml), the combined organic phases washed with brine, dried with sodium sulfate, filtered and evaporated under reduced pressure providing the title compound as a single diastereomer: 90 g (65% yield without recovery of the starting ketone IV), m.p. 182-184° C. The NMR data were identical with published in Synth. Commun. 2009, 39, 1611 for (2S,3R)-enantiomer.

From the aqueous phase the unreacted 1-(2,4-difluorophenyl)-2-(1H-1,2,4-triazol-1-yl)ethanone (IV) was isolated by evaporation of the aqueous phase under reduced pressure and re-crystallization of the residue from isopropanol: 30 g.

Example 10

3-(2,5-difluorophenyl)-3-hydroxy-2-methyl-4-(1H-1,2,4-triazol-1-yl)butanenitrile To a solution of diisopropylamine (11 g) in dry THF (100 ml) 1.6 M solution of butyllithium in hexane (63 ml) was slowly added at −78° C. under nitrogen atmosphere. The mixture was allowed to warm up to −30° C., then re-cooled to −78° C. before propionitrile (5.4 g) was slowly added (exothermic reaction, cooling). The mixture was stirred at this temperature for ca. 15 min, 1-(2,5-difluorophenyl)-2-(1H-1,2,4-triazol-1-yl)ethanone (10 g) was added, the reaction mixture warmed up to −20° C. within ca. 1 hr and finally poured on aqueous solution of phosphate buffer (pH 7). The aqueous phase was extracted 3 times with ethylacetate (300 ml) and the combined organic phase was twice with water, dried with sodium carbonate, filtered and evaporated under reduced pressure providing the title compound: 9 g. The analytical data were identical with published in U.S. Pat. No. 6,300,353 and WO99/45008 for (2S,3R)-enantiomer.

Example 11

3-(2,4-dichlorophenyl)-3-hydroxy-2-methyl-4-(1H-1,2,4-triazol-1-yl)butanenitrile Similar as described in Example 10 the title compound was obtained in 25% yield based on a scale of 10 g., m.p. 164° C.

Example 12

3-(2,5-difluorophenyl)-3-hydroxy-2-methyl-4-(1H-1,2,4-triazol-1-yl)thiobutyramide To a solution of diisoproplylamine (120 g) in dry THF (1500 ml) 1.6 M solution of butyllithium in hexane (730 ml) was slowly added at −40° C. under nitrogen atmosphere. The mixture was allowed to warm up to −20° C. for ca. 10 min, then re-cooled to −78° C. and to this LDA-solution N,N-bis (2,4-dimethoxybenzyl)thiopropionamide (390 g), dissolved in dry THF (500 ml) was slowly added that the reaction temperature did not exceed −40° C. (exothermic reaction, cooling). After addition the mixture was stirred at −40° C. for ca. 1 hr, then at this temperature 1-(2,5-difluorophenyl)-2-(1H-1,2,4-triazol-1-yl)ethanone (223 g), dissolve in dry THF (400 ml), was slowly added, the reaction mixture stirred for another 2 hrs, then within ca. 1 hr warmed up to −20° C. and finally poured on an aqueous phosphate buffer solution (pH 7). The aqueous phase was extracted 3 times with ethylacetate (500 ml) and the combined organic phases dried twice with sodium carbonate, filtered and evaporated under reduced pressure providing 3-(2,5-difluorophenyl)-3-hydroxy-2-methyl-4-(1H-1,2,4-triazol-1-yl)-N,N-bis(2,4-dimethoxybenzyl)thiobutyramide: 590 g (96% yield) as a single diastereomer. This crude material was dissolved at 0° C. under cooling in a mixture of methylenechloride (1000 ml) and triflic acid (150 g) and slowly triethylsilane (500 g) was added within ca. 3 hrs keeping the temperature under 10° C. After the reduction was finished the reaction mixture was poured very slowly on aqueous saturated sodium bicarbonate solution, extracted 3 times with ethylacetate (500 ml), dried with sodium sulphate, filtered and evaporated under reduced pressure providing the crude title compound: 250 g (80% yield). The analytical data were identical with published one for (2R,3R)-enantiomer in U.S. Pat. No. 6,300,353 and WO99/45008.

Example 13

3-(2,4-difluorophenyl)-3-hydroxy-2-methyl-4-(1H-1,2,4-triazol-1-yl)thiobutyramide To a solution of diisoproplylamine (120 g) in dry THF (1500 ml) a 1.6M solution of butyllithium in hexane (730 ml) was slowly added at −40° C. under nitrogen atmosphere. The mixture was allowed to warm up to −20° C. for ca. 30 min, then re-cooled to −78° C. and to this LDA solution N,N-diallyl-thiopropionamide (169 g), dissolved in dry THF (300 ml) was slowly added that the reaction temperatures did not exceed −40° C. (exothermic reaction, cooling). After this addition the mixture was stirred at −40° C. for ca. 30 min, then at this temperature 1-(2,4-difluorophenyl)-2-(1H-1,2,4-triazol-1-yl)ethanone (223 g) dissolve in dry THF (400 ml) was slowly added, the reaction mixture stirred for another 3 hrs, then within ca. 1 hr warmed up to −20° C. and then poured on an aqueous phosphate buffer solution (pH 7). The aqueous phase was extracted 3 times with ethylacetate (1000 ml) and the combined organic phase dried with sodium carbonate, filtered and evaporated under reduced pressure providing 3-(2,4-difluorophenyl)-3-hydroxy-2-methyl-4-(1H-1,2,4-triazol-1-yl)-N,N-diallylthiobutyramide: 250 g (63% yield) as almost a single diastereomer. This crude compound was converted in the title compound e.g. as given in Example 12 providing the title compound: 130 g (41% yield), m.p. 164-167° C. The analytical data were identical with published data for (2R,3R)-enantiomer (U.S. Pat. No. 5,648,372 and Chem. Pharm. Bull. 1998, 46, 623-630).

The invention claimed is:
1. A process for the preparation of enantiomerically pure compound of general forumla (I), having the 2R, 3R configuration,

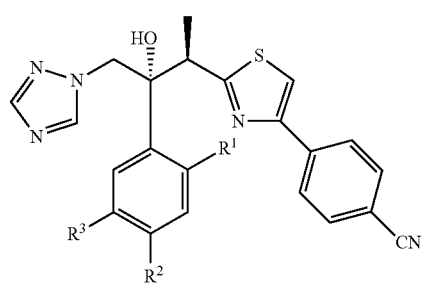

I wherein $R^1$, $R^2$ and $R^3$ represent, independently from one another, hydrogen, fluorine or $CF_3$-group;
which comprises
either
a) a resolution step of the racemic compound of formula (I), having the 2R/S, 3R/S configuration, by adding a chiral acid, crystallizing the mixture, collecting the desired diastereomeric salt of formula (I) either from the precipitate or from mother liquid and then converting the salt of formula (I) into an enantiomerically pure from of the compound of formula (I) by treatment with an appropriate organic or inorganic base or using an ion-exchange resin;

or
b) a resolution step of the racemic compound of formula (II), having the 2R/S, 3R/S configuration,

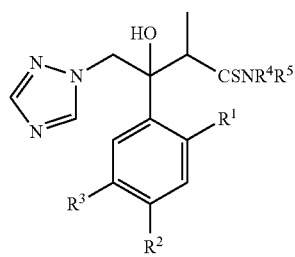

II wherein $R^1$, $R^2$ and $R^3$ are the same as defined for compound of formula (I) and wherein $R^4$ and $R^5$ represent, independently from one another, hydrogen, alkyl, aryl, alkylaryl, arylalkyl, alkoxy, aryloxy, arylalkoxy, alkylaryloxy, trialkylsilyl, alkylarylsilyl, mono-, di- or trimethoxybenzyl, or another for nitrogen known protective group, wherein $R^4$ and $R^5$ can also form together aliphatic or aromatic heterocyclic ring system;
by adding a chiral acid, crystallizing the mixture, collecting the desired diastereomeric salt of formula (II), having the 2R,3R configuration, either from the precipitate or from mother liquid and then converting the salt of formula (II) into an enantiomerically pure form of the compound of formula (II) by treatment with an organic or inorganic base or an ion-exchange resin, or alternatively using the salt of formula (II) directly, and after removal of the nitrogen protective groups $R^4$ and $R^5$ in case $R^4$ and $R^5$ are not hydrogens, reacting the enantiomerically pure form of the compound of formula (II) with 2-chloro-4'-cyanoacetophenone;
or
c) a resolution step of the racemic compound of formula (III), having the 2S/R, 3R/S configuration,

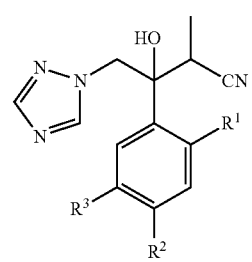

III wherein $R^1$, $R^2$ and $R^3$ are the same as defined for the compound of formula (I);
by adding a chiral acid, crystallizing the mixture, collecting the desired diastereomeric salt of formula (III), having the 2S,3R configuration, either from the precipitate or from mother liquid and then converting the salt of formula (III) into an enantiomerically pure form of the compound (III) by treatment with an organic or inorganic base or an ion-exchange resin, or using the enantiomerically pure form of the salt of formula (III) directly, and reacting with hydrogen sulfide followed by reaction of the resulting enantiomerically pure form of the compound of formula (II) with 2-chloro-4'-cyanoacetophenone.
2. A process according to claim 1, wherein the chiral acid is (1R or 1S)-10-camphorsulfonic acid or (D or L)-tartaric acid or (D or L)-dibenzoyl tartaric acid, (1R or 1S)-3-bromocamphor-10-sulfonic acid, (R or S)-1,1'-binaphtyl-2,2'-diyl-hydrogenphosphate.

3. A process according to claim 1, wherein the chiral acid is (1R or 1S)-10-camphorsulfonic acid.

4. A process for the preparation of enantiomerically pure compound of formula (I), having the 2R,3R configuration,

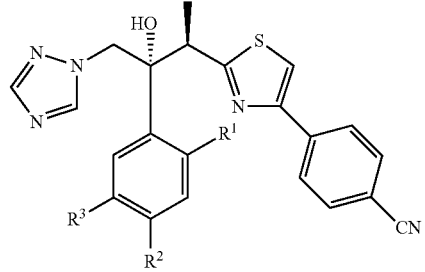

wherein $R^1$, $R^2$ and $R^3$ represent, independently from one another, hydrogen, fluorine or $CF_3$-group, comprising a resolution step of the racemic compound of formula (I), having the 2R/S, 3R/S configuration, by adding a chiral acid, crystallizing the mixture,
collecting the desired diastereomeric salt of formula (I) either from the precipitate or from mother liquid and converting the salt of formula (I) into an enantiomerically pure form of the compound of formula (I) by treatment with an organic or inorganic base or an ion-exchange resin.

5. A process according to any one of claims 1 and 4, wherein in compound of formula (I), (II) and (Ill), $R^1$ and $R^2$ represent fluorine and $R^3$ represents hydrogen.

6. A process according to any one of claims 1 and 4, wherein in compound of formula (I), (II) and (Ill), $R^1$ and $R^3$ represent fluorine and $R^2$ represents hydrogen.

* * * * *